United States Patent [19]

Hansen et al.

[11] Patent Number: 5,315,016

[45] Date of Patent: May 24, 1994

[54] PROCESS FOR PREPARING PURE PODOPHYLLOTOXIN

[75] Inventors: Henrik F. Hansen, Roedovre; Kim Kjoernaes, Vaerloese, both of Denmark

[73] Assignee: Nycomed Dak A/S, Copenhagen S, Denmark

[21] Appl. No.: 960,102

[22] Filed: Oct. 13, 1992

[51] Int. Cl.$^5$ ............................................. C07D 307/77
[52] U.S. Cl. .................................................... 549/298
[58] Field of Search ........................................ 549/298

[56] References Cited

U.S. PATENT DOCUMENTS 4,680,399  7/1987  Buchardt ............................. 546/139
5,057,616  10/1991  Jennings et al. ..................... 549/298

OTHER PUBLICATIONS

Beutner et al., "Treatment of Genital Warts", Seminars in Dermatol., vol. 9, Jun. 1990, pp. 148–151.

Issell, "The Podophyllotoxin Derivatives VP16-213 and VM26", Cancer Chemother Pharmacol, vol. 7, 1982, pp. 73–80.

Buchardt et al., "Thermal Chemistry of Podophyllotoxin in Ethanol and a Comparison of the Cytostatic Activity of the Thermolysis Products", Journal of Pharmaceutical Sciences, vol. 75, No. 11, Nov. 1986, pp. 1076–1080.

Schrecker, et al., "Components of Podophyllotoxin", XVIII. Polymorphic Modifications of Podophyllotoxin, Journal Org. Chem., vol. 21, 1956, pp. 288–291.

Andersen, et al., "Inclusion Complexes with Podophyllotoxin, Structural Characterization and Chiral Recognition", J. Chem. Soc., Perkin Trans., vol. 2, 1990, pp. 1871–1979.

Dunstan, et al., "A Chemical Investigation of the Constituents of Indian and American Podophyllum (Podophyllum emodi and Podophyllum peltatum)", J. Chem. Soc., vol. LXXIII, 1898, p. 209.

Primary Examiner—C. Warren Ivy
Assistant Examiner—A. A. Owens
Attorney, Agent, or Firm—Foley & Lardner

[57] ABSTRACT

A process for preparing crystalline, anhydrous podophyllotoxin from a podophyllotoxin product comprises dissolving the product in a non-aromatic and non-halogenated solvent which has a boiling point at atmospheric pressure not exceeding 130° C., and which contains at the most about 1% v/v of water, cooling the solution to precipitate crystals of podophyllotoxin, isolating the crystals and drying them at a temperature which during the drying procedure is increased but is always such that it is below the temperature at which the crystals sinter or melt, the drying being continued until the melting point is in a range of 183°–184° C. and the residual amount of solvent is at the most 500 ppm. When the starting material contains complexed or adsorbed organic solvent, an initial azeotropic evaporation treatment is performed to remove this solvent. The yield of pure podophyllotoxin is greatly increased by adding water to the crystallization mixture.

52 Claims, No Drawings

PROCESS FOR PREPARING PURE PODOPHYLLOTOXIN

FIELD OF THE INVENTION

The present invention relates to a process for preparing crystalline, anhydrous podophyllotoxin of high purity from podophyllotoxin-containing products such as podophyllotoxin hydrates, inclusion complexes or solvates of podophyllotoxin with organic solvents, and podophyllotoxin phases which have organic solvents adsorbed or occluded thereto.

BACKGROUND OF THE INVENTION

Podophyllotoxin is a well-known lignan which has been isolated from plant extracts, particularly from so-called Podophyllum resins obtained by solvent extraction of various parts—notably the roots and rhizomes—of plants of the genus Podophyllum, e.g. the North American species *Podophyllum peltatum* and the Indian species *Podophyllum emodi*.

Podophyllotoxin has proved to be a highly effective chemotherapeutic agent for the treatment of venereal warts (condylomata acuminata; also known as genital warts) [see, e.g., R. K. Beutner and G. von Krog, *Seminars in Dermatol.* 9 (1990) 148]. Another important current use of podophyllotoxin is as a starting material for the synthesis of the anti-cancer drugs known as VP 16-213 ("etoposide") and VM 26 ("teniposide") [see, e.g., B. F. Issell, *Cancer Chemother. Pharmacol.* 7 (1982) 73].

The use of podophyllotoxin as a drug in its own right, and as a starting material for the preparation of other important drugs, has led to considerable interest in the preparation of podophyllotoxin in pure form, and the patent literature contains a number of references, e.g. U.S. Pat. No. 4,680,399 (to Buchardt) and U.S. Pat. No. 5,057,616 (to Jennings et al.), relating hereto.

Podophyllotoxin has been reported to occur in a variety of polymorphic forms having different melting points, and in the form of various solvates [see, e.g., A. W. Schrecker et al., *J. Org. Chem.* 21 (1956) 288]. Thus, Schrecker et al. (in the latter reference) recognized at least four crystalline modifications of podophyllotoxin, viz.: A, with water (m.p. 161°–162° C.); B, unsolvated (m.p. 183°–184° C.); C, with water and benzene of crystallization (m.p. 114°–118° C. "foaming"); and D, unsolvated (m.p. 188°–189° C.).

Podophyllotoxin has also been found to retain not only water alone, but also water together with certain organic solvents—notably simple aromatic and heteroaromatic molecules, e.g. benzene, toluene, nitrobenzene, chlorobenzene, phenol and pyridine—in the crystal structure as so-called complexes (also known as "host-guest complexes" or "inclusion complexes") or solvates see, e.g., U.S. Pat. No. 4,680,399 and K. V. Andersen et al., *J. Chem. Soc. Perkin Trans.* 2 (1990) 1871. The ratio between podophyllotoxin, organic solvent and water in such complexes is frequently 2:1:2; thus, for example and by way of illustration, the crystalline toluene complex (which has the latter composition) contains approximately 100,000 ppm of toluene.

Andersen et al. (in the latter reference) have demonstrated by X-ray diffraction that unsolvated podophyllotoxin ($C_{22}H_{22}O_8$) has a melting point in the range of 182°–184° C., and that podophyllotoxin semihydrate ($C_{22}H_{22}O_8 \cdot 0.5H_2O$) melts in the range of 162°–164° C.

Furthermore, and of particular significance in relation to the present invention (vide infra), a number of organic solvents become tenaciously adsorbed to or occluded on the surface of crystals of podophyllotoxin, and this has been confirmed by the present inventors for, for example, halogenated lower alkanes such as dichloromethane and chloroform. Moreover, this tenacity is often such that simple recrystallisation of such podophyllotoxin products having adsorbed solvent molecules using other solvents, e.g. alcohols, generally does not lead to satisfactory removal of the adsorbed solvent. The present inventors have found that the mere fact that a particular product exhibits a melting point in the correct range for pure, crystalline, anhydrous, solvent-free podophyllotoxin is no guarantee for the absence of adsorbed or occluded solvent, since a number of podophyllotoxin products with significant contents of absorbed halocarbon solvent have been found to exhibit the correct melting point interval for completely pure podophyllotoxin.

Failure on the part of various past investigators to recognize the occurrence of these various forms, solvates and "solvent adsorbates" has resulted in considerable confusion, as well as misinterpretation of results. Furthermore, and rather significantly from a pharmaceutical viewpoint, important patent literature methods for the preparation of podophyllotoxin, such as those described in U.S. Pat. No. 4,680,399 and U.S. Pat. No. 5,057,616, disclose the use of, inter alia, halocarbon solvents at a late stage in the isolation procedure, there being no disclosure in these documents to indicate any awareness of the fact that (as mentioned above) such solvents are tanaciously retained by crystals of (otherwise pure) podophyllotoxin.

U.S. Pat. No. 5,057,616 discloses (see column 5, lines 62-65) that the allegedly pure product produced by precipitation from a halocarbon solvent (such as dichloromethane) and subsequent recrystallization from, typically, a ketone/ether mixture "may have a somewhat low melting point", necessitating the use of a rather elaborate and time-consuming further crystallization and vacuum-drying procedure to arrive at a product displaying the correct melting point. In U.S. Pat. No. 4,680,399, which initially exploits the crystallization properties of podophyllotoxin complexes with simple aromatic and heteroaromatic molecules (yide supra) in a first stage of isolation of podophyllotoxin from Podophyllum resin, podophyllotoxin of "especially high purity" is isolated by simple recrystallization (from a solvent such as ethyl acetate or aqueous ethanol) of a product obtained, for example, from a chloroform solution of such a complex.

What appears to be the first reported attempt to prepare pure, anhydrous podophyllotoxin was made by W. R. Dunstan and T. A. Henry [*J. Chem. Soc.* (1898) 209] by recrystallization of a podophyllotoxin hydrate from "absolute ethanol". However, the crystals obtained by allowing the solvent to evaporate in "a vacuous desiccator" melted at 157° C., and recrystallization of these crystals from alcohol by adding water resulted in podophyllotoxin in hydrated form. These authors go on to describe the preparation of "anhydrous podophyllotoxin" by heating the "hydrated substance" at its melting point (117° C.) for a few minutes, dissolving the resulting product in dry chloroform, and adding light petroleum until the mixture became slightly turbid. Upon standing, the "anhydrous podophyllotoxin" crystallized.

Schrecker et al. [*J. Org. Chem.* 21 (1956) 288] describe the preparation of "unsolvated" (unhydrated) podophyllotoxin by a procedure involving heating hydrated podophyllotoxin at 137° C. in a vacuum. However, not only is this method impracticable for the large scale preparation of anhydrous podophyllotoxin, but based on present knowledge it is apparent that prolonged treatment of podophyllotoxin at the elevated temperature in question will, owing to the thermolability of podophyllotoxin at such temperatures, at least lead to significant epimerisation [see, e.g., O. Buchardt et al., *J. Pharm. Sci.* 75 (1986) 1076].

On the basis of the above discussion, it is clear that there is a need for a straightforward method for the preparation—from any readily available intermediate podophyllotoxin product, such as a hydrate, an inclusion complex with an organic solvent, or another solvent-containing podophyllotoxin phase—of anhydrous podophyllotoxin which is of high and reproducible purity, and which is free of pharmaceutically unacceptable organic solvents. The present invention fulfils this need.

DESCRIPTION OF THE INVENTION

The present invention thus provides a process for preparing crystalline, anhydrous podophyllotoxin from a podophyllotoxin product which may be a podophyllotoxin hydrate, an inclusion complex or solvate of podophyllotoxin with an organic solvent, or a podophyllotoxin phase having one or more organic solvents adsorbed or occluded thereto, the process comprising the steps of:

I)

in those cases where said podophyllotoxin product is an inclusion complex or solvate of podophyllotoxin with an organic solvent, or a podophyllotoxin phase having one or more organic solvents adsorbed or occluded thereto:

dissolving the podophyllotoxin product in a first non-aromatic and non-halogenated organic solvent which forms an azeotrope with the organic solvent(s) present in the inclusion complex or the podophyllotoxin phase, and then evaporating the solvent from the resulting solution at a temperature not exceeding 130° C.,

II)

subjecting the product thus obtained to repetition of the dissolution/evaporation procedure of step I),

III)

dissolving the podophyllotoxin product, in the form in which it is present at this stage, in a second non-aromatic and non-halogenated solvent which has a boiling point at atmospheric pressure not exceeding 130° C., and which contains at the most about 1% v/v of water,

IV)

cooling the resulting solution to precipitate crystals of podophyllotoxin, the cooling being continued until precipitation of crystals has substantially ceased,

V)

isolating the precipitated crystals, and

VI)

drying the isolated crystals at a temperature which during the drying procedure is increased but is always such that it is below the temperature at which the crystals sinter or melt, the drying being continued until the melting point is in a range of 183°–184° C. and the residual amount of solvent is at the most 500 ppm.

Podophyllotoxin hydrates which are suitable for use as starting materials in the process of the invention are, for example, podophyllotoxin semihydrate (vide supra) or other hydrates which have been reported in the literature, e.g. podophyllotoxin dihydrate.

Inclusion complexes or solvates which are suitable for use as starting materials in the process according to the invention include complexes of those types already discussed above, such as complexes containing aromatic or heteroaromatic molecules (e.g. benzene, toluene, o-, m- and p-xylene, chloro-, bromo- or nitrobenzene, phenol, pyridine or any of the other aromatic and heteroaromatic molecules disclosed, for example, in U.S. Pat. No. 4,680,399 for use as complexing agents) or non-aromatic molecules (e.g. 2-butanol).

Suitable podophyllotoxin phases having adsorbed or occluded organic solvents are, for example, materials of the types referred to and employed in the working examples provided herein, such as materials containing adsorbed haloalkanes (e.g. chloro-substituted lower alkanes such as chloroform, dichloromethane or dichloroethane).

As should be apparent on the basis of the discussion given earlier, above, the role of the dissolution/evaporation procedure which is carried out initially in the process of the invention when the podophyllotoxin-containing starting material is an inclusion complex or is a material containing adsorbed or occluded organic solvent is to remove the solvent(s) associated with the podophyllotoxin via the formation of an azeotrope with a first solvent which in itself is non-aromatic and non-halogenated.

Whilst it may be sufficient in certain cases to carry out this dissolution/azeotropic evaporation procedure once, it will normally be appropriate to subject the podophyllotoxin product in question to a total of at least two, or even three, such procedures (i.e. at least one or two repetitions of the dissolution/evaporation procedure) to ensure adequate removal of the complex-forming or adsorbed organic solvent(s). By ensuring, as in the process of the invention, that the temperature during the azeotropic evaporation does not exceed 130° C., the risk of formation of, e.g., epimerization products of podophyllotoxin is minimized.

In some cases, particularly for first non-aromatic and non-halogenated solvents of relatively low boiling point, simply boiling the solution at atmospheric pressure has proved to be a suitable method for evaporating at least most of the solvent from the solution of the podophyllotoxin product therein, and in this case—for the reasons already outlined—it is clear that the solvent in question should have a boiling point at atmospheric pressure which does not exceed 130° C. It is more preferable, however, that the boiling point does not exceed 100° C.

Alternatively, and generally preferably, the solvent may be removed by evaporation under reduced pressure, e.g. using a rotary evaporator or the like; evaporation under reduced pressure in this manner may also suitably be employed to essentially complete the removal of the solvent remaining after the bulk thereof has been removed by boiling the solution. In this case the solvent per se may of course, if appropriate, have a boiling point at atmospheric pressure which exceeds 130° C.

Suitable first non-aromatic and non-halogenated solvents are to be found, for example, among monohydric, straight-or branched-chain $C_1$–$C_5$ alkanols (alcohols), carboxylic acid esters containing up to 5 carbon atoms, and cyclic ethers containing 4 or 5 carbon atoms.

More specifically, suitable first non-aromatic and non-halogenated solvents may be selected among the following: $C_1$–$C_5$ alkanols such as methanol, ethanol, 1-propanol, 2-propanol, 1-butanol, 2-butanol, 2-pentanol, 3-pentanol, and tert-pentyl alcohol; monocarboxylic acid esters such as ethyl acetate, 1-propyl acetate, 2-propyl acetate, 1-butyl acetate, sec-butyl acetate, tert-butyl acetate, methyl propionate and ethyl propionate; and cyclic ethers such as tetrahydrofuran and tetrahydropyran.

As already mentioned, the second non-aromatic and non-halogenated solvent should, in general, have a water content not exceeding about 1% by volume (v/v). Certain solvents having slightly higher water contents, e.g. about 2%, may prove to be suitable for the purpose of the invention, but as a general rule it will clearly be preferable that the solvent in question has as low a water content as possible, in order to obviate any risk of crystallisation of a hydrate, such as podophyllotoxin semihydrate (abbreviated PX.½$H_2O$ in the present specification). For example, a particularly suitable solvent in this context is absolute ethanol (cf. the working examples provided herein), which is generally obtainable in a quality containing $\leq$0.5% v/v of water.

In general, the second non-aromatic and non-halogenated solvent will suitably be chosen among monohydric, straightor branched-chain $C_2$–$C_5$ alkanols (alcohols), carboxylic acid esters containing up to 5 carbon atoms, and cyclic ethers containing 4 or 5 carbon atoms. Thus, it will in many cases be possible to employ one and the same solvent as the first and second non-aromatic and non-halogenated solvents.

Experiments have indicated that the simplest monohydric alkanol, i.e. methanol, is not well suited for use as the second non-aromatic and non-halogenated solvent. Likewise, tests indicate that a number of other potential candidates, including acetone (a ketone) and acetonitrile, are also unsuited for this purpose. Whilst it thus seems unlikely on this basis that lower ketones or nitriles in general will be practicable for use as the second non-aromatic and non-halogenated solvent, it is nevertheless possible that they may be applicable as first non-aromatic and non-halogenated solvents.

Specific examples of suitable second non-aromatic and non-halogenated solvents may be selected among the following: $C_2$–$C_5$ alkanols such as ethanol, 1-propanol, 2-propanol, 1-butanol, 2-butanol, 2-pentanol, 3-pentanol and tert-pentyl alcohol; monocarboxylic acid esters such as ethyl acetate, 1-propyl acetate, 2-propyl acetate, 1-butyl acetate, sec-butyl acetate, tert-butyl acetate, methyl propionate and ethyl propionate; and cyclic ethers such as tetrahydrofuran and tetrahydropyran.

Dissolution of the podophyllotoxin product in the second non-aromatic and non-halogenated solvent is appropriately achieved with heating at a temperature which does not exceed the boiling point at atmospheric pressure of the solvent in question, and the heating temperature should preferably not exceed 100° C. for a number of solvents, it has proved very suitable to dissolve the podophyllotoxin product with heating at a temperature of about 65° C.

It has been found to be advantageous, particularly from the point of view of ease of subsequent volatilization of the second non-aromatic and non-halogenated solvent in the final stages of the process of the invention, that the solvent has a boiling point at atmospheric pressure which does not exceed 110° C., and which more preferably does not exceed 100° C.; when dissolution of the podophyllotoxin product in the solvent takes place with heating at the boiling point of the solvent, it is also an advantage that the boiling point of the solvent does not exceed 110° C., more preferably does not exceed 100° C., since this minimizes (for reasons already mentioned) any risk of formation of epimerisation products or other breakdown products.

From a practical viewpoint it is generally advantageous that the second non-aromatic and non-halogenated solvent is either fully miscible with water, or at least exhibits a significant degree of miscibility with water, for example such that the solvent in question is capable of dissolving water to an extent of at least 10% v/v. It is further advantageous that this level of miscibility also applies at temperatures around 0° C.

In order to precipitate podophyllotoxin crystals from the solution in the second non-aromatic and non-halogenated solvent, it has been found to be advantageous to cool the solution to a temperature of about 0° C., e.g. by employing a water-ice mixture. To ensure that no crystallization of the solvent itself can take place under these conditions, the solvent should have a freezing point below the temperature of the cooling bath, e.g. suitably below −5° C., and preferably even lower, such as below −30° C.

Whilst the basic process of the invention as disclosed above leads to good yields of crystalline, anhydrous podophyllotoxin of high purity, it has importantly—and very surprisingly—been found that a very considerable improvement in the yield of anhydrous podophyllotoxin may be achieved by adding water to the mixture of solvent and crystals obtained by cooling in the prescribed manner, and then subjecting the resulting mixture to further cooling until further precipitation of crystals has substantially ceased. It appears that the presence of large amounts of seed crystals of anhydrous podophyllotoxin in the cooled mixture prior to addition of water ensures that formation of the anhydrous form continues after addition of water, in spite of the presence of relatively large amounts of added water. Thus, whereas, for example, final yields of an hydrous podophyllotoxin of typically about 80% (based on the podophyllotoxin content of the starting product employed) are obtainable starting from hydrated podophyllotoxin and without adding water in the manner described above, the addition or water can lead to almost quantitative yields, typically 96–98% (cf. the working examples herein).

The amount of water which should be added in the manner cutlined above does not seem to be very critical, and a volume of water equal to the volume of the second non-aromatic and non-halogenated solvent may, for example, suitably be employed. It has been found that a solvent:water volume ratio of about 1:2 generally gives very satisfactory results, and this applies even in cases where water and the second non-aromatic and non-halogenated solvent in question are not completely miscible in these proportions (such as in the case of ethyl acetate as solvent; cf. the working examples herein).

The drying procedure employed in the method according to the invention is very suitably performed, for example, as a two-stage procedure in which the isolated crystals of podophyllotoxin are first subjected to a pre-drying step wherein the crystals are dried at a relatively low temperature, after which they are subjected to a final drying step wherein they are dried at a higher temperature.

Nevertheless, it is important that the previously mentioned condition, viz. that the temperature at any stage of drying is always below the melting point of the crystals at that stage, is fulfilled. This has in general been found to be the case when the crystals of podophyllotoxin are pre-dried at a temperature between 20° C. and the boiling point at atmospheric pressure of the second non-aromatic and non-halogenated organic solvent, until the melting point of the pre-dried crystals exceeds 120° C.

The further drying of the crystals should then preferably take place at a temperature between the boiling point of the second non-aromatic and non-halogenated organic solvent at atmospheric pressure and 130° C., until the melting point of the crystals is in the range of 183°–184° C. and the residual amount of the solvent adhering to, or otherwise associated with, the crystals (determined, for example, by gas chromatographic analysis of samples) is at the most 500 ppm.

The temperature for the pre-drying stage should preferably be in the range of 25°–50° C., and a temperature of about 40° C. appears, in general, to be particularly suitable. Predrying at about 40° C. for a period of about 24 hours appears, in general, to give excellent results, although for certain solvents, e.g. 1- and 2-propanol, 1-butanol and ethyl acetate, a shorter drying period at this temperature (such as about 8 hours) appears to be sufficient. It should, however, be mentioned here that the melting point of crystals prepared using certain solvents, exemplified by tetrahydrofuran, after drying at about 40° C. may not quite attain 120° C., even though the dried crystals at this stage are suitable for further drying at the higher temperature in accordance with the process of the invention.

The temperature for the further drying of the crystals should preferably be in the range of 105°–115° C., and a temperature of about 110° C. appears, in general, to be especially suitable, particularly when carried out for a period of about 24 hours.

As will be apparent from the disclosure herein, it is not necessary to carry out the dissolution/azeotropic evaporation procedure when the podophyllotoxin product used as starting material in the process according to the invention is a podophyllotoxin hydrate. Thus, in a particularly preferred embodiment of the process of the invention the podophyllotoxin product is a podophyllotoxin hydrate (such as PX.½H₂O), and the process comprises the steps of:

A) dissolving the podophyllotoxin hydrate in absolute ethanol at a temperature of about 65° C.,
B) cooling the resulting solution at about 0° C. to precipitate crystals of podophyllotoxin, the cooling being continued until precipitation of crystals of podophyllotoxin has substantially ceased,
C) adding water to the mixture from step B) and further cooling the resulting mixture at a temperature of about 0° C., until further precipitation of crystals of podophyllotoxin has substantially ceased,
D) isolating the precipitated crystals of podophyllotoxin,
E) pre-drying the isolated crystals of podophyllotoxin at a temperature of about 40° C. for 24 hours, and
F) further drying the pre-dried crystals of podophyllotoxin at a temperature of about 110° C. for 24 hours.

The invention is further illustrated by the following non-limiting examples.

The apparatus employed for the various measurements made in connection with the working examples described below was as follows:

$^1$H NMR and $^{13}$C NMR spectra were recorded on a Brucker AM 250 spectrometer.

IR spectra of compounds (in potassium bromide discs) were recorded on a Perkin-Elmer 500 spectrometer.

Melting points were determined using a Reichart melting point microscope.

Optical rotation was determined using an AA 10 polarimeter from OBtical active.

Product purity was determined by High-Performance Liquid Chromatography (HPLC) using a Spectra Physics 8000 instrument with a Spherisorb S5 ODS column and employing an eluent consisting of methanol, 0.09M potassium dihydrogen phosphate (pH 6.5) and acetonitrile (10:9:1) at a flow rate of 1 ml/min.

Residual amounts of solvents (see Examples 10–16, below) were determined by gas chromatography (GC) using a Varian 3400 gas chromatograph as follows:

For alkane and halogenated alkane solvents:

Sample volume: 1 µl of an acetone solution (100.0 mg of the podophyllotoxin product in question made up to 1.00 ml with acetone)

GC standards: appropriate dilutions of a standard solution of 5 µl chloroform and 5 µl dichloromethane made up to 100.00 ml in acetone.

Column: TENAX 60–80 mesh (1.8 m × 3 mm i.d.)
Carrier gas: nitrogen
Carrier gas flow rate: 30 ml/min
Temperature: injection: 150° C.; oven: 100° C.; detector: 250° C.
Detection: Electron capture detector employing $\beta$-particle-emitting radioactive nickel isotope ($^{63}$Ni).

For aromatic solvents:

Sample volume: 1 µl of an acetone solution (100.0 mg of the podophyllotoxin product in question made up to 1.00 ml with acetone).

GC standards: appropriate dilutions of a standard solution of 5 µl absolute ethanol and 5 µl toluene made up to 100.00 ml in acetone.

Column: PORAPAK Q 80–100 mesh (1.8 m × 4 mm i.d.).
Carrier gas: nitrogen.
Carrier gas flow rate: 40 ml/min.
Temperature: injection: 150° C.; oven: 230° C.; detector: 250° C.
Detection: Flame ionization detector.

EXAMPLES 1–9

Preparation of anhydrous podophyllotoxin from hydrated podophyllotoxin

Example 1

Podophyllotoxin semihydrate (PX.½H₂O) of melting point 162° C. [700 g; obtained from podophyllum resin by crystallization from aqueous ethanol in the manner described by Schrecker et al., *J. Org. Chem.* 21 (1956) 288] was dissolved in absolute ethanol (1400 ml; containing ≦0.5% v/v of water) in a flask with heating to ca. 65° C. with stirring for 20 min. The resulting solution was cooled in ice-water, whereupon crystalline material precipitated. When precipitation had substantially ceased, distilled water (2100 ml) was added with stirring. The resulting mixture was allowed to stand with cooling in ice-water for 2 hours. The crystalline precipitate was isolated by filtration on a sintered glass funnel (D2) and washed on the filter with ice-cold ethanol/water (1:2 v/v). The crystals were dried in a drying oven at 40° C. for 24 hours and then at 110° C. for a further 24 hours. The resulting anhydrous podophyllotoxin (686 g) had a melting point of 183°-184° C. and a purity of >99% according to HPLC. $[\alpha]_{20}^D = -133.4°$ (c=1, CHCl$_3$).

The $^1$H NMR, $^{13}$C NMR and IR spectra of the product were identical with those reported in the literature [see e.g. Buchardt et al., *J. Pharm. Sci.* 75 (1986) 1076].

Examples 2-9

Anhydrous podophyllotoxin was prepared in a manner analogous to that described in Example 1 using the solvents listed in Table 1A below. Each of the listed solvents contained ≦1% v/v of water. 7 g of PX.½H$_2$O was used as starting material in each case. Ice-cold ethanol/water was employed for the final washing on the filter (as in Example 1), although subsequent experiments indicate that washing with a mixture of the solvent in question and water generally gives satisfactory results.

In order to further illustrate the importance of a low water content in the solvent employed, Table 1A and 1B further include results obtained using 99% v/v ethanol (i.e. water content 1% v/v) and 96% v/v ethanol (i.e. water content 4% v/v), respectively. The product obtained in Example 9 using 96% v/v ethanol as the solvent (melting point 163°-165° C.) was the semihydrate (cf. the discussion elsewhere in the present specification).

Table 1A gives details of the solvents and volumes thereof employed, the volume of water added to complete crystallization in each case, and the yield and melting point of the anhydrous podophyllotoxin product prepared in each case.

Table 1B gives the initial melting points of each of the prepared podophyllotoxin phases after air drying but prior to drying at 40° C., the duration of drying at 40° C., the melting point of each product after drying at 40° C., and the duration of drying at 110° C.

TABLE 1A

| Ex. | Solvent, ml | ml water* | Yield/% | M.p./°C. |
|---|---|---|---|---|
| 2 | 1-Propanol, 12 | 24 | 97 | 183-184 |
| 3 | 2-Propanol, 17 | 34 | 98 | 183-184 |
| 4 | 1-Butanol, 15 | 30 | 97 | 183-184 |
| 5 | 2-Butanol, 15 | 30 | 98 | 183-184 |
| 6 | Ethyl acetate, 8 | 16 | 97 | 183-184 |
| 7 | THF#, 7 | 14 | 96 | 183-184 |
| 8 | Ethanol (99%), 7 | 7 | 96 | 183-184 |
| 9 | Ethanol (96%), 7 | 7 | 97 | 163-165§ |

*Water added after initial crystallization;
Tetrahydrofuran.
§Podophyllotoxin semihydrate

TABLE 1B

| Ex. | M.p./°C. (air-dried) | Drying time/h (40° C.) | M.p./°C. (40° C. drying) | Drying time/h (110° C.) |
|---|---|---|---|---|
| 2 | 115-117 | 8 | 181-182 | 24 |
| 3 | 117-119 | 8 | 181-182 | 24 |
| 4 | 116-118 | 8 | 181-183 | 24 |
| 5 | 118-120 | 24 | 122-124 | 24 |
| 6 | 118-120 | 8 | 181-182 | 24 |
| 7 | 116-118 | 24 | 116-118 | 24 |
| 8 | 117-119 | 24 | 120-121 | 24 |
| 9 | 117-118 | 24 | 162-164 | 48 |

EXAMPLES 10-16

Preparation of anhydrous podophyllotoxin from podophyllotoxin products containing organic solvents Example 10

Podophyllotoxin:toluene:water inclusion complex [1:0.5:1; 700 g; prepared according to Andersen et al., *J. Chem. Soc. Perkin Trans.* 2 (1990) 1871] was dissolved in 96% (v/v) ethanol (2000 ml) in a flask with heating to ca. 65° C. with stirring for 20 min. The solvent was then removed by evaporation under reduced pressure (15 mmHg) at ca. 55° C. The resulting product was redissolved in 96% (v/v) ethanol (1500 ml) in the same manner as described above, and the solvent was again removed by evaporation under reduced pressure as before. After one further repetition of the latter redissolution/evaporation procedure, the residue was dissolved in absolute ethanol with heating at ca. 65° C.

The resulting solution was cooled in ice-water, whereupon crystalline material precipitated. When precipitation was substantially complete, distilled water (2100 ml) was added with stirring. The resulting mixture was allowed to stand with cooling in ice-water for 2 hours. The crystalline precipitate was isolated by filtration on a sintered glass funnel (D2) and washed on the filter with ice-cold ethanol/water (1:2 v/v). The crystals were dried in a drying oven at 40° C. for 24 hours and then at 110° C. for a further 24 hours. The resulting anhydrous podophyllotoxin (678 g) had a melting point of 183°-184° C. and a purity of >99% according to HPLC. $[\alpha]_{20}^D = -134.1°$ (c=1, CHCl$_3$).

The $^1$H NMR, $^{13}$C NMR and IR spectra of the product were identical with those reported in the literature (cf. Example 1, above).

EXAMPLES 11-16

Anhydrous podophyllotoxin was prepared in a manner analogous to that described in Example 10, starting from various podophyllotoxin products containing the residual organic solvents listed in Table 2 below and employing the dissolution solvents specified therein. Table 2 also gives the yield and melting point for the anhydrous podophyllotoxin product obtained in each case.

Podophyllotoxin products containing residual benzene or hexane/benzene were prepared by the method described by Schrecker et al., *J. Org. Chem.* 21 (1956) 288 (products B and C2 therein). Podophyllotoxin products containing residual methylene chloride or chloroform were obtained in an analogous manner by precipitation from methylene chloride and chloroform solutions, respectively, of another podophyllotoxin product (e.g. PX.½H$_2$O, or a podophyllotoxin product containing e.g. hexane and/or benzene).

7 g of podophyllotoxin product was used in each case, and the solvent and the washing medium were employed in the same relative amounts as in Example 10.

In all cases, the final product contained less than 25 ppm of the original residual organic solvent, as demonstrated by GC.

TABLE 2

| Example | Residual solvent,[#] ppm | Solvent employed | Yield/% | M.p./°C. |
|---|---|---|---|---|
| 11 | $CH_2Cl_2$, 2030 | ethanol[*] | 89 | 183.3 |
| 12 | $CHCl_3$, 1570 | ethanol[*] | 90 | 183.4 |
| 13 | benzene, 1750 | ethanol[*] | 89 | 183.5 |
| 14 | benzene, 1750 | methanol[§] | 90 | 183.3 |
| 15 | hexane/benzene, 1100/1530 | ethanol[*] | 87 | 183.6 |
| 16 | hexane/benzene, 1100/1530 | methanol[§] | 89 | 183.4 |

[#]Residual solvent present in starting material;
[*]96% ethanol for azeotropic evaporation procedure; absolute ethanol for final precipitation procedure; 96% ethanol for washing procedure.
[§]Analytical grade methanol for azeotropic evaporation procedure; absolute ethanol for final precipitation procedure; 96% ethanol for washing procedure.

We claim:

1. A process for preparing crystalline, anhydrous podophyllotoxin from a podophyllotoxin product selected from the group consisting of podophyllotoxin hydrates, inclusion complexes or solvates of podophyllotoxin with organic solvents, and podophyllotoxin phases having organic solvents adsorbed or occluded thereto, the process comprising the steps of:

I) in those cases where said podophyllotoxin product is a product selected from complexes or solvates of podophyllotoxin with organic solvents, and podophyllotoxin phases having organic solvents adsorbed or occluded thereto:
dissolving said podophyllotoxin product in a first non-aromatic and non-halogenated organic solvent which forms an azeotrope with the organic solvent present in said inclusion complex or said podophyllotoxin phase, and then evaporating the solvent from the resulting solution at a temperature not exceeding 130° C., II) where appropriate the product thus obtained to repetition of the dissolution/evaporation procedure of step I), III) dissolving the podophyllotoxin product of steps I or II, or alternatively the hydrate, in the form in which it is present at this stage, in a second non-aromatic and non-halogenated solvent which has a boiling point at atmospheric pressure not exceeding 130° C., and which contains at the most about 1% v/v of water, IV) cooling the resulting solution to precipitate crystals of podophyllotoxin, the cooling being continued until precipitation of crystals has substantially ceased, V) isolating the precipitated crystals, and VI) drying the isolated crystals at a temperature which during the drying procedure is increased but is always such that it is below the temperature at which the crystals sinter or melt, the drying being continued until the melting point is in a range of 183°–184° C. and the residual amount of solvent is at the most 500 ppm.

2. A process according to claim 1, comprising the further step of adding water to the mixture resulting from step IV) and further cooling the thus-obtained mixture until further precipitation of crystals has substantially ceased.

3. A process according to claim 1, wherein at least two said repetitions of the dissolution/evaporation procedure of step I) are carried out in step II).

4. A process according to claim 1, wherein said podophyllotoxin product is (i) a complex or a solvate of podophyllotoxin with an organic solvent or (ii) a podophyllotoxin phase to which an organic solvent is adsorbed or occluded, and wherein said evaporation of said solvent in step I) comprises boiling the solution at atmospheric pressure.

5. A process according to claim 1, wherein said podophyllotoxin product is (i) a complex or solvent of podophyllotoxin with an organic solvent or (ii) a podophyllotoxin phase to which an organic solvent is adsorbed or occluded, and wherein said evaporation of said solvent in step I) is carried out under reduced pressure.

6. A process according to claim 1, wherein said podophyllotoxin product is (i) a complex or solvate of podophyllotoxin with an organic solvent or (ii) a podophyllotoxin phase to which an organic solvent is adsorbed or occluded, and wherein said first non-aromatic and non-halogenated solvent has a boiling point at atmospheric pressure which does not exceed 130° C.

7. A process according to claim 1, wherein said podophyllotoxin product is (i) a complex or solvate of podophyllotoxin with an organic solvent or (ii) a podophyllotoxin phase to which an organic solvent is adsorbed or occluded, and wherein said first non-aromatic and non-halogenated solvent is selected from the group consisting of: monohydric $C_1$–$C_5$ alkanols; carboxylic acid esters containing up to 5 carbon atoms; and cyclic ethers containing 4 or 5 carbon atoms.

8. A process according to claim 1, wherein said podophyllotoxin product is (i) a complex or solvate of podophyllotoxin with an organic solvent or (ii) a podophyllotoxin phase to which an organic solvent is adsorbed or occluded, and wherein said first non-aromatic and non-halogenated solvent is selected from the group consisting of: methanol, ethanol, 1-propanol, 2-propanol, 1-butanol, 2-butanol, 2-pentanol, 3-pentanol, tert-pentyl alcohol; ethyl acetate, 1-propyl acetate, 2-propyl acetate, 1-butyl acetate, sec-butyl acetate, tert-butyl acetate, tetrahydrofuran and tetrahydropyran.

9. A process according to claim 1, wherein said second non-aromatic and non-halogenated solvent is capable of dissolving water to an extent of at least 10% v/v.

10. A process according to claim 1, wherein said second non-aromatic and non-halogenated solvent has a boiling point at atmospheric pressure which does not exceed 110° C.

11. A process according to claim 1, wherein said second non-aromatic and non-halogenated solvent has a freezing point below −5° C.

12. A process according to claim 1, wherein said second non-aromatic and non-halogenated solvent has a freezing point below −30° C.

13. A process according to claim 1, wherein said second non-aromatic and non-halogenated solvent is selected from the group consisting of: monohydric $C_2$–$C_5$ alkanols; carboxylic acid esters containing up to 5 carbon atoms; and cyclic ethers containing 4 or 5 carbon atoms.

14. A process according to claim 1, wherein said second non-aromatic and non-halogenated solvent is selected rom the group consisting of: ethanol, 1-propanol, 2-propanol, 1-butanol, 2-butanol, 2-pentanol, 3-pentanol, tert-pentyl alcohol; ethyl acetate, 1-propyl acetate, 2-propyl acetate, 1-butyl acetate, sec-butyl acetate, tert-butyl acetate; tetrahydrofuran and tetrahydropyran.

15. A process according to claim 1, wherein said podophyllotoxin product is (i) a complex or solvate of podophyllotoxin with an organic solvent or (ii) a podophyllotoxin phase to which an organic solvent is adsorbed or occluded, and wherein said first and said second non-aromatic and non-halogenated solvent are the same.

16. A process according to claim 1, wherein the podophyllotoxin product in step III) is dissolved with heating at a temperature not exceeding the boiling point atmospheric pressure of said second non-aromatic and non-halogenated solvent.

17. A process according to claim 1, wherein the podophyllotoxin product in step III) is dissolved with heating at a temperature not exceeding 100° C.

18. A process according to claim 1, wherein the podophyllotoxin product in step III) is dissolved with heating at a temperature of about 65° C.

19. A process according to claim 1, wherein the solution from step III) is cooled in step IV) to a temperature of about 0° C.

20. A process according to claim 1, wherein said drying procedure in step VI) comprises the steps of
 a) pre-drying the crystals of podophyllotoxin at a temperature between 20° C. and the boiling point at atmospheric pressure of said second non-aromatic and non-halogenated organic solvent until the melting point of the pre-dried crystals exceeds 120° C., and
 b) further drying the pre-dried crystals of podophyllotoxin at a temperature between the boiling point of said second non-aromatic and non-halogenated organic solvent at atmospheric pressure and 130° C. until the melting point of the crystals is in the range of 183°–184° C. and the residual amount of solvent associated therewith is at the most 500 ppm.

21. A process according to claim 1 wherein said drying procedure in step VI) comprises the steps of
 a) pre-drying the crystals of podophyllotoxin at a temperature between 25° C. and 50° C. until the melting point of the pre-dried crystals exceeds 120° C., and
 b) further drying the pre-dried crystals of podophyllotoxin at a temperature between the boiling point of said second non-aromatic and non-halogenated organic solvent at atmospheric pressure and 130° C. until the melting point of the crystals is in the range of 183°–184° C. and the residual amount of solvent associated therewith is at the most 500 ppm.

22. A process according to claim 1, wherein said drying procedure in step VI) comprises the steps of
 a) pre-drying the crystals of podophyllotoxin at a temperature of about 40° C. until the melting point of the pre-dried crystals exceeds 120° C., and
 b) further drying the pre-dried crystals of podophyllotoxin at a temperature between the boiling point of said second non-aromatic and non-halogenated organic solvent at atmospheric pressure and 130° C. until the melting point of the crystals is in the range of 183°–184° C. and the residual amount of solvent associated therewith is at the most 500 ppm.

23. A process according to claim 1, wherein said drying procedure in step VI) comprises the steps of
 a) pre-drying the crystals of podophyllotoxin at a temperature between 20° C. and the boiling point of said second non-aromatic and non-halogenated organic solvent at atmospheric pressure until the melting point of the pre-dried crystals exceeds 120° C., and
 b) further drying the pre-dried crystals of podophyllotoxin at a temperature in the range of 105°–115° C. until the melting point of the crystals is in the range of 183°–184° C. and the residual amount of solvent associated therewith is at the most 500 ppm.

24. A process according to claim 1, wherein said drying procedure in step VI) comprises the steps of
 a) pre-drying the crystals of podophyllotoxin at a temperature between 20° C. and the boiling point of said second non-aromatic and non-halogenated organic solvent at atmospheric pressure until the melting point of the pre-dried crystals exceeds 120° C., and
 b) further drying the pre-dried crystals of podophyllotoxin at a temperature of about 110° C. until the melting point of the crystals is in the range of 183°–184° C. and the residual amount of solvent associated therewith is at the most 500 ppm.

25. A process according to claim 1, wherein said podophyllotoxin product is a podophyllotoxin hydrate, the process comprising the steps of:
 A) dissolving said podophyllotoxin hydrate in absolute ethanol at a temperature of about 65° C.,
 B) cooling the resulting solution at about 0° C. to precipitate crystals of podophyllotoxin, the cooling being continued until precipitation of crystals of podophyllotoxin has substantially ceased,
 C) adding water to the mixture from step B) and further cooling the resulting mixture at a temperature of about 0° C., until further precipitation of crystals of podophyllotoxin has substantially ceased,
 D) isolating the precipitated crystals of podophyllotoxin,
 E) pre-drying the isolated crystals of podophyllotoxin at a temperature of about 40° C. for 24 hours, and
 F) further drying the pre-dried crystals of podophyllotoxin at a temperature of about 110° C. for 24 hours.

26. A process according to claim 2, wherein said podophyllotoxin product is a (i) a complex or a solvate of podophyllotoxin with an organic solvent or (ii) a podophyllotoxin phase to which an organic solvent is adsorbed or occluded, and wherein said evaporation of said solvent in step I) comprises boiling the solution at atmospheric pressure.

27. A process according to claim 2, wherein said podophyllotoxin product is (i) a complex or solvate of podophyllotoxin with an organic solvent or (ii) a podophyllotoxin phase to which an organic solvent is adsorbed or occluded, and wherein said evaporation of said solvent in step I) is carried out under reduced pressure.

28. A process according to claim 2, wherein said podophyllotoxin product is (i) a complex or solvate of podophyllotoxin with an organic solvent or (ii) a podophyllotoxin phase to which an organic solvents is adsorbed or occluded, and wherein said first non-aromatic and non-halogenated solvent has a boiling point at atmospheric pressure which does not exceed 130° C.

29. A process according to claim 2, wherein said podophyllotoxin product is (i) a complex or solvate of podophyllotoxin with an organic solvent or (ii) a podophyllotoxin phase to which an organic solvent is adsorbed or occluded, and wherein said first non-aromatic and non-halogenated solvent is selected from the group consisting of: monohydric $C_1$-$C_5$ alkanols; carboxylic acid esters containing up to 5 carbon atoms; and cyclic ethers containing 4 or 5 carbon atoms.

30. A process according to claim 2, wherein said podophyllotoxin product is (i) a complex or solvate of podophyllotoxin with an organic solvent or (ii) a podophyllotoxin phase to which an organic solvent is adsorbed or occluded, and wherein said first non-aromatic and non-halogenated solvent is selected from the group consisting of: methanol, ethanol, 1-propanol, 2-propanol, 1-butanol, 2-butanol, 2-pentanol, 3-pentanol, tert-pentyl alcohol; ethyl acetate, 1-propyl acetate, 2-propyl acetate, 1-butyl acetate, sec-butyl acetate, tert-butyl acetate, tetrahydrofuran and tetrahydropyran.

31. A process according to claim 2, wherein said second non-aromatic and non-halogenated solvent is capable of dissolving water to an extent of at least 10% v/v.

32. A process according to claim 2, wherein said second non-aromatic and non-halogenated solvent has a boiling point at atmospheric pressure which does not exceed 110° C.

33. A process according to claim 2, wherein said second non-aromatic and non-halogenated solvent has a freezing point below −5° C.

34. A process according to claim 2, wherein said second non-aromatic and non-halogenated solvent has a freezing point below −30° C.

35. A process according to claim 2, wherein said second non-aromatic and non-halogenated solvent is selected from the group consisting of: monohydric $C_2$-$C_5$ alkanols; carboxylic acid esters containing up to 5 carbon atoms; and cyclic ethers containing 4 or 5 carbon atoms.

36. A process according to claim 2, wherein said second non-aromatic and non-halogenated solvent is selected from the group consisting of: ethanol, 1-propanol, 2-propanol, 1-butanol, 2-butanol, 2-pentanol, 3-pentanol, tert-pentyl alcohol; ethyl acetate, 1-propyl acetate, 2-propyl acetate; 1-butyl acetate, sec-butyl acetate, tert-butyl acetate; tetrahydrofuran and tetrahydropyran.

37. A process according to claim 2, wherein said podophyllotoxin product is (i) a complex or solvate of podophyllotoxin with an organic solvent or (ii) a podophyllotoxin phase to which an organic solvent is adsorbed or occluded, and wherein said first and said second non-aromatic and non-halogenated solvent are the same.

38. A process according to claim 2, wherein the podophyllotoxin product in step III) is dissolved with heating at a temperature not exceeding the boiling point at atmospheric pressure of said second non-aromatic and non-halogenated solvent.

39. A process according to claim 2, wherein the podophyllotoxin product in step III) is dissolved with heating at a temperature not exceeding 100° C.

40. A process according to claim 2, wherein the podophyllotoxin product in step III) is dissolved with heating at a temperature of about 65° C.

41. A process according to claim 2, wherein the solution from step III) is cooled in step IV) to a temperature of about 0° C.

42. A process according to claim 2, wherein said drying procedure in step VI) comprises the steps of
a) pre-drying the crystals of podophyllotoxin at a temperature between 20° C. and the boiling point at atmospheric pressure of said second non-aromatic and non-halogenated organic solvent until the melting point of the pre-dried crystals exceeds 120° C., and
b) further drying the pre-dried crystals of podophyllotoxin at a temperature between the boiling point of said second non-aromatic and non-halogenated organic solvent at atmospheric pressure and 130° C. until the melting point of the crystals is in the range of 183°–184° C. and the residual amount of solvent associated therewith is at the most 500 ppm.

43. A process according to claim 2, wherein said drying procedure in step VI) comprises the steps of
a) pre-drying the crystals of podophyllotoxin at a temperature between 25° C. and 50° C. until the melting point of the pre-dried crystals exceeds 120° C., and
b) further drying the pre-dried crystals of podophyllotoxin at a temperature between the boiling point of said second non-aromatic and non-halogenated organic solvent at atmospheric pressure and 130° C. until the melting point of the crystals is in the range of 183°–184° C. and the residual amount of solvent associated therewith is at the most 500 ppm.

44. A process according to claim 2, wherein said drying procedure in step VI) comprises the steps of
a) pre-drying the crystals of podophyllotoxin at a temperature of about 40° C. until the melting point of the pre-dried crystals exceeds 120° C., and
b) further drying the pre-dried crystals of podophyllotoxin at a temperature between the boiling point of said second non-aromatic and non-halogenated organic solvent at atmospheric pressure and 130° C. until the melting point of the crystals is in the range of 183°–184° C. and the residual amount of solvent associated therewith is at the most 500 ppm.

45. A process according to claim 2, wherein said drying procedure in step VI) comprises the steps of
a) pre-drying the crystals of podophyllotoxin at a temperature between 20° C. and the boiling point of said second non-aromatic and non-halogenated organic solvent at atmospheric pressure until the melting point of the pre-dried crystals exceeds 120° C., and
b) further drying the pre-dried crystals of podophyllotoxin at a temperature in the range of 105°–115° C. until the melting point of the crystals is in the range of 183°–184° C. and the residual amount of solvent associated therewith is at the most 500 ppm.

46. A process according to claim 2, wherein said drying procedure in step VI) comprises the steps of
a) pre-drying the crystals of podophyllotoxin at a temperature between 20° C. and the boiling point of said second non-aromatic and non-halogenated organic solvent at atmospheric pressure until the melting point of the pre-dried crystals exceeds 120° C., and b) further drying the pre-dried crystals of podophyllotoxin at a temperature of about 110° C. until the melting point of the crystals is in the range of 183°–184° C. and the residual amount of solvent associated therewith is at the most 500 ppm.

47. A process according to claim 2, wherein said podophyllotoxin product is a podophyllotoxin hydrate, the process comprising the steps of:
    A) dissolving said podophyllotoxin hydrate in absolute ethanol at a temperature of about 65° C.,
    B) cooling the resulting solution at about 0° C. to precipitate crystals of podophyllotoxin, the cooling being continued until precipitation of crystals of podophyllotoxin has substantially ceased,
    C) adding water to the mixture from step B) and further cooling the resulting mixture at a temperature of about 0° C., until further precipitation of crystals of podophyllotoxin has substantially ceased,
    D) isolating the precipitated crystals of podophyllotoxin,
    E) pre-drying the isolated crystals of podophyllotoxin at a temperature of about 40° C. for 24 hours, and
    F) further drying the pre-dried crystals of podophyllotoxin at a temperature of about 110° C. for 24 hours.

48. A process according to claim 1, wherein in step II) the product is subjected to repetition of said dissolution/evaporation procedure.

49. A process according to claim 2, wherein in step II) the product is subjected to repetition of said dissolution/evaporation procedure.

50. A process according to claim 1, wherein step II) is not performed, such that only one of the dissolution/evaporation procedures of step I) is performed.

51. A process according to claim 2, wherein step II) is not performed, such that only one of the dissolution/evaporation procedures of step I) is performed.

52. A process according to claim 2, wherein at least two said repetitions of the dissolution/evaporation procedure of step I) are carried out in step II).

* * * * *

UNITED STATES PATENT AND TRADEMARK OFFICE
CERTIFICATE OF CORRECTION

PATENT NO. : 5,315,016
DATED : May 24, 1994
INVENTOR(S) : Hansen et al.

It is certified that error appears in the above-indentified patent and that said Letters Patent is hereby corrected as shown below:

Column 8, lines 44 and 45, "$^\beta$-particle-emitting" should read --$\beta$-particle-emitting--.

Column 12, Claim 5, lines 2 and 3, "(i) a complex or solvent of podophyllotoxin . . ." should read --(i) a complex or solvate of podophyllotoxin . . .--.

Signed and Sealed this

Sixth Day of December, 1994

Attest:

BRUCE LEHMAN

*Attesting Officer*　　*Commissioner of Patents and Trademarks*

UNITED STATES PATENT AND TRADEMARK OFFICE
CERTIFICATE OF CORRECTION

PATENT NO. : 5,315,016
DATED : May 24, 1994
INVENTOR(S) : Hansen et al.

It is certified that error appears in the above-indentified patent and that said Letters Patent is hereby corrected as shown below:

On the title page item [73], "Nycomed Dak A/S"
Should read --NYCOMED DAK A/S--.

Signed and Sealed this

Tenth Day of January, 1995

Attest:

BRUCE LEHMAN

Attesting Officer

Commissioner of Patents and Trademarks